(12) United States Patent
Talaga et al.

(10) Patent No.: US 7,320,874 B2
(45) Date of Patent: Jan. 22, 2008

(54) ASSAYING THE TEICHOIC ACIDS OF GRAM+ BACTERIA

(75) Inventors: Philippe Talaga, Sainte Consorce (FR); Patricia Sepulcri, Marcy l'Etoile (FR); Sandrine Vialle-Blanc, Tassin la Demi Lune (FR)

(73) Assignee: Aventis Pasteur SA, Lyons (FR)

( * ) Notice: Subject to any disclaimer, the term of this patent is extended or adjusted under 35 U.S.C. 154(b) by 0 days.

(21) Appl. No.: 10/885,219

(22) Filed: Jul. 6, 2004

(65) Prior Publication Data

US 2005/0009121 A1   Jan. 13, 2005

Related U.S. Application Data

(60) Provisional application No. 60/497,653, filed on Aug. 25, 2003.

(30) Foreign Application Priority Data

Jul. 8, 2003   (FR)   .................. 03 08305

(51) Int. Cl.
*G01N 33/569* (2006.01)
*C07K 1/12* (2006.01)

(52) U.S. Cl. ..................... 435/7.32; 530/343

(58) Field of Classification Search .................. None
See application file for complete search history.

(56) References Cited

U.S. PATENT DOCUMENTS

| 4,686,102 A | 8/1987 | Ritchey et al. ............... 424/92 |
| 5,665,561 A | 9/1997 | Tuomanen et al. ........... 435/34 |
| 2002/0119166 A1 | 8/2002 | Pier et al. |

OTHER PUBLICATIONS

CarboPac PA1 and PA10 Columns for Mono-and Disaccharide Analysis, Dionex 2000, pp. 1-8.□□http://www.dionex.com.*
Hawley. The Condensed Chemical Dictionary, (1981) p. 759.*
Fischer et al., "Teichoic acid and lipoteichoic acid of *Streptococcus pneumoniae* possess identical chain structures, A reinvestigation of teichoid acid (C polysaccharide)," Eur. J. Biochem. 215, 851-857 (1993).
Jennings and Lugowski, "Facile cleavage of some 2-acetamido-2-deoxy-β-D-gluco-and galactopyranosides using aqueous HF[1]", National Research Council of Canada, Jun. 1980, 2610-2612.
Jennings et al., "Structure of the Complex Polysaccharide C-Substance from *Streptococcus pneumoniae* Type 1", Biochemistry 1980, 4712-4719.
Jones and Currie, Control of Components of Bacterial Polysaccharide Vaccines by Physical Methods, Biologicals 1991, 19 (41-47).
Karlsson et al., The pneucococcal commom antigen C-polysaccharide occurs in different forms, Eur. J. Biochem 1999, 265, 1091-1097.
Talaga, et al., "Quantitative determination of C-polysaccharide in *Streptococcus pneumoniae* capsular polysaccharies by use of high-performance anion-exchange chromatography with pulsed amperometric detection", Vaccine 19 (2001) 2987-2994.
Talaga, et al., "Development of a high-performance anion-exchange chromatography with pulsed-amperometric detection based quantification assay for pneumococcal polysaccharides and conjugates", Vaccine 20 (2002) 2474-2484.
Hyun Han et al., "Pneumacoccal Lipoteichoic Acid (LTA) Is Not as Potent as Staphylococcal LTA in Stimulating Toll-Like Receptor 2", Infection and Immunity, Oct. 2003, p. 5541-5548.2003.

* cited by examiner

*Primary Examiner*—Jon Weber
*Assistant Examiner*—Paul Martin
(74) *Attorney, Agent, or Firm*—McDonnell Boehnen Hulbert & Berghoff LLP

(57) ABSTRACT

The invention relates to a method for assaying the teichoic acids present, most commonly in residual form, in a preparation of Gram+ bacterial antigens. This method requires, first of all, a controlled hydrolysis with hydrofluoric acid at a temperature of less than or equal to 40° C., in order to release the oligosaccharides specific for teichoic acids. The assaying of the specific oligosaccharides can then be carried out by various techniques, in particular by high performance chromatography coupled with pulsed amperometric detection (HPAEC-PAD). The method according to the invention can in particular be used to assay the residual amounts of teichoic acids present in preparations containing capsular polysaccharides of *Streptococcus pneumoniae*, which may be useful as vaccines.

25 Claims, 2 Drawing Sheets

ASSAYING THE TEICHOIC ACIDS OF GRAM+ BACTERIA

Figure 1:
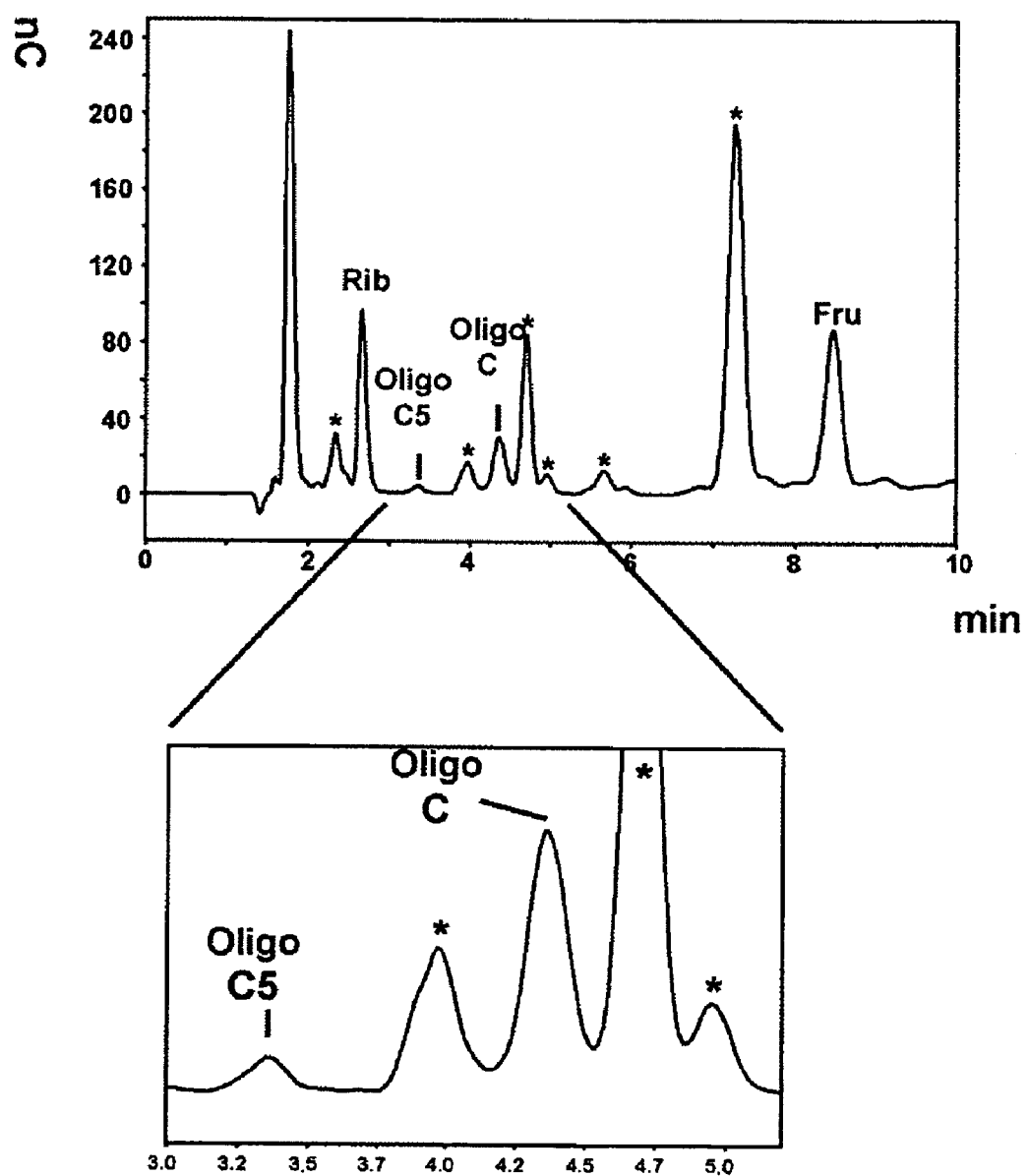

This application claims the benefit of U.S. Provisional Application No. 60/497,653 Filed Aug. 25, 2003.

The invention relates to a method for assaying teichoic acids, in particular in a preparation, which comes from a Gram+ bacterial culture.

Teichoic acids are known to be constituents of the complex constituting the membrane and the wall of Gram+ bacteria. They are in close contact with the peptidoglycan of the wall. Covalent bonds reinforce this link. Teichoic acids, which have in their chemical structure a lipid or a glycolipid end can anchor themselves in the outer membrane via hydrophobic bonds.

There are mainly two types of teichoic acids:

The first type gathers teichoic acids, which are linear polymers of ribitol phosphate or glycerol phosphate linked themselves by phosphodiester bonds. Free hydroxyl groups of ribitol or glycerol can be substituted by residues such as amino acid residues, N acetyl glucosamine, or N acetyl galactosamine. These teichoic acids are referred as "alcohol polymers".

the second type gathers teichoic acids, which are polysaccharides having a chain of repeating units. The repeating unit generally consists of a chain of at least two monosaccharides followed by a ribitol phosphate or a glycerol phosphate. The phosphate group is involved in the linking together of the repeating units by means of phosphodiester bonds. Free hydroxyl groups of the repeating units can also be substituted by different residues.

Moreover, among teichoic acids, there are lipoteichoic acids, which have an additional lipid or glycolipd chain. This additional part is linked to the terminal ribitol phosphate or to the terminal glycerol phosphate by a phosphodiester bond. The lipid part is usually a monoacyl or diacyl glycerol chain.

According to the bacterial species, the teichoic acids are of "alcohol polymer type" like in the case of *Staphylococcus aureus*, or of "polysaccharide type" like in the case of *Streptococcus pneumonaie*. In this species, two ubiquitous teichoic acids are known: the C-polysaccharide and lipoteichoic acid (also referred to as Forssman antigen).

The C-polysaccharide consists of a chain of repeating units, each made up of four monosaccharide residues, a glucopyranose (Glcp) residue, a 2-acetamido-4-amino-2,4,6-trideoxy-D-galactose (AAT) residue and two N-acetyl galactopyranose (GalpNAc) residues, followed by a ribitol-5-phosphate (ribitol-5-P) residue. At least one of the two GalpNAc residues is substituted with phosphocholine (P-Cho). The structural formula of this repeating unit is as follows:

ubstituted repeating units in varying proportion. These proportions vary in particular as a function of the culturing conditions and of the pneumococcal serotype.

As regards the lipoteichoic acid, it has the primary structure of the C-polysaccharide associated with a glycolipid, of formula β-D-Glcp(1-4)-β-D-AAT (1-3)-α-D-Glcp(1-3) acyl$_2$Gro, in which Glcp denotes a glucopyranose residue, AAT denotes a 2-acetamido-4-amino-2,4,6-trideoxy-D-galactose, acyl denotes a fatty acid residue and Gro denotes a glycerol residue. This glycolipid is attached, via a phosphodiester bond, to the terminal ribitol of the chain.

Some Gram+ bacteria, such as *Streptococcus pneumonaie*, have a capsule and/or are responsible for serious infections. Vaccines consisting of capsule polysaccharides in purified form exist against *Streptococcus pneumonaie*. The methods used to purify the capsular polysaccharides eliminate as much as possible the polysaccharides from the wall (teichoic acid). In fact, although they are very immunogenic, teichoic acids are weakly protective and their presence in a vaccine needlessly increases the antigenic load. Furthermore, teichoic acids can trigger undesirable inflammatory reactions (Infection and Immunity (2003), 71:5541)

According to the requirements of the health authorities, the content of a high quality vaccine must be characterized with precision. It must be possible to assay not only the vaccine antigen, but also all the possible contaminants, among which are the teichoic acids, in particular with regard to capsular polysaccharide-based vaccines. The assaying of the contaminants is all the more difficult and tricky since it relates to very small quantities. Assaying methods must therefore be sensitive, efficient and specific.

The latter requirement of specificity is particularly difficult to respect. In fact, strong structural similarities exist between the teichoic acids of "polysaccharide type" and the capsular polysaccharides. For example, as regards *Streptococcus pneumonaie*, the repeating unit of the C-polysaccharide contains a phosphate group just like that of the capsular polysaccharides of the serotypes 6B, 10A, 11A, 15B, 17F, 18C, 19A, 19F, 20, 23F. The phosphate group of the repeating unit of the C-polysaccharide is directly involved in the linking together of the repeating units via a phosphodiester bond, as are those of the capsular polysaccharides of serotype 6B, 10A, 17F, 19A, 19F and 20. The capsular polysaccharides of serotypes 6B and 10A are those which exhibit the strongest similarity with the pneumococcal teichoic acids since they have a ribitol phosphate involved in the linking together of the repeating units.

Jones C. et al., have described, in Biologicals (1991) 19: 41, a method for assaying the C-polysaccharide by nuclear magnetic resonance (NMR). This method evaluates the resonance of the N-methyl radical of the phosphocholine groups of the C-polysaccharide. This technique is not pre-

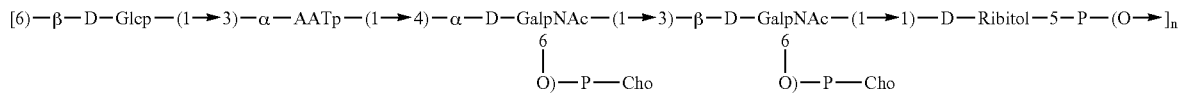

C. Karlsson et al., Eur. J. Biochem. (1999) 265: 1091 have shown that the repeating unit can exist in two forms: (i) a form disubstituted with two phosphocholine residues, as represented above; and (ii) a form monosubstituted with a single phosphocholine residue. Consequently, the C-polysaccharide chain contains monosubstituted and discise since, as indicated above, the proportion of phosphocholine groups is not constant.

Talaga P. et al. propose, in Vaccine (2000) 19: 2987, an assaying method based on quantification of the ribitol released during hydrolysis of the C-polysaccharide subsequent to two successive treatments: the first with hydrofluoric acid (HF) at 48% for 2 hours at 65° C., the second with 2N trifluoroacetic acid for 2 hours at 120° C. This double treatment brings about cleavage of the oside bonds. The hydrolysate contains essentially monosaccharides. The ribitol is then separated from the other constituents by high performance anion exchange chromatography (HPAEC) on a CarboPac™ MA1 analytical chromatography column, using, for the elution, a 480 mM isocratic sodium hydroxide solution. The ribitol is then quantified by a pulsed amperometric detection (PAD) system. Even though this technique for assaying ribitol allows a correct and sensitive evaluation of the amount of C-polysaccharide, it is incompatible with the presence, in the medium, of a capsular polysaccharide which contains ribitol.

Now, some capsular polysaccharides of interest in vaccines contain ribitol. As has just been seen, these are, for example, the capsular polysaccharides of serotype 6B and 10A of *Streptococcus pneumonaie*. The technique of Talaga et al. is not therefore suitable for assaying teichoic acids in a preparation that contains those serotypes, e.g. in the commercial pneumococcus vaccines.

Briefly, the methods for assaying teichoic acids of polysaccharide type, which are known to date, have drawbacks. No method yet exists which is precise, sensitive, reliable and applicable to any preparation, which comes from a gram+ bacterial culture.

The present invention overcomes this shortage by proposing a novel method for assaying teichoic acids of "polysaccharide type". This method searches for the oligosaccharides specific for teichoic acids released through cleavage of the phosphodiester bonds, during treatment with hydrofluoric acid (HF), according to the method of Jennings & Lugowski, Can. J. Chem. (1980) 58: 2610. When the repeating unit contains a β-D GalpNac molecule or a β-D GlcpNac molecule linked to a ribitol phosphate or a glycerol phosphate, a secondary cleavage may also occur with the release of ribitol or glycerol. In other words, depending on the structure of the teichoic acid, the specific oligosaccharide will be substantially identical to the repeating unit or else will differ therefrom by the loss of ribitol or glycerol.

Thus, in the case of the C-polysaccharide, the specific oligosaccharide has the formula:

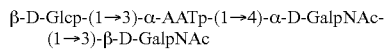

β-D-Glcp-(1→3)-α-AATp-(1→4)-α-D-GalpNAc-(1→3)-β-D-GalpNAc

After hydrolysis, specific oligosaccharides then remain which are subsequently separated from one another and assayed.

Furthermore, it is indicated, in the interests of thoroughness, that this definition applies mutatis mutandis to the oligosaccharides specific for capsular polysaccharides having repeating units incorporating phosphate groups involved in the chain, such as the polysaccharides of pneumococcal serotypes 6B, 10A, 17F, 19A, 19F and 20.

Thus, a subject of the present invention is a method for assaying the teichoic acids of "polysaccharide type" in a preparation, which comes from a Gram+ bacterial culture, according to which:
 (i) the preparation is treated with hydrofluoric acid (HF) at a temperature of less than or equal to 40° C., in order to release the oligosaccharides specific for the teichoic acids present in the preparation; and
 (ii) the specific oligosaccharides obtained in (i) are assayed.

The term "preparation which comes from a Gram+ bacterial culture", is intended to mean: (i) a preparation of whole bacteria; (ii) a lysate of bacteria which can be obtained by chemical detergents (desoxycholate, tween, ether, ect. . . . ) or by mechanical processes such as osmotic shock, or sonication; (iii) a bacterial fraction obtained, for example, by fractionated alcohol precipitation; (iv) a culture supernatant of Gram+ bacteria; and (v) a preparation comprising one or more components (antigens) of Gram+bacteria, in a purified form.

Preferably, the Gram+ bacteria preparation is a culture supernatant or a preparation of purified antigen(s). The treatment with hydrofluoric acid (HF) is advantageously carried out at a temperature ranging from −70° C., to 40° C., preferably ranging from 0° C. to 20° C., even more preferably between 4° C. and 10° C. In general, the higher the temperature, the lower the selectivity of action of the hydrofluoric acid on the phosphodiester bonds. For this reason, it is important not to exceed 40° C.

Typically, the hydrofluoric acid is used at a final concentration of between 10 and 73% (weight/weight), limits included; preferably between 40 and 60%; entirely preferably between 45 and 50%; e.g. at a concentration of 48%.

The duration of treatment with hydrofluoric acid is not critical. It is inversely proportional to the temperature. Those skilled in the art are capable of adjusting this duration as a function of the temperature chosen and of the concentration at which the hydrofluoric acid is used. However, it is indicated that, the higher the temperature, the shorter the duration of treatment must be in order to ensure as much as possible the integrity of the oside bonds. In general, it is preferable for the treatment not to exceed 96 hours. When the temperature is between 20 and 40° C., a duration of treatment not exceeding 1 hour is recommended; between 0 and 10° C., a duration of treatment not exceeding 2 hours is recommended. Conversely, when the temperature is less than 0° C., the duration of treatment may exceed 24 hours.

Good results are obtained when the HF is used at a concentration of 48%, at 4° C. for 48 hours. Under these conditions, the rate of recovery of the specific oligosaccharide can reach 90% of the theoretical value. To assay the teichoic acid-specific oligosaccharide(s) obtained after treatment with HF, it is advantageously advisable to separate it or them from the other constituents and to characterize it or them. Separation, characterization and quantification can be carried out according to various techniques, e.g. biochemical techniques, available to those skilled in the art. It is indicated, however, that methods known to allow the separation and/or the assaying of monosaccharides are most particularly suitable.

According to a particular method, use is made of a high performance anion exchange chromatography (HPAEC) technique, optionally coupled with pulsed amperometric detection (PAD).

To this end, a suitable chromatography support should allow good resolution and should be compatible with a medium having a very high pH (≧12). In practice, under these pH conditions, the support should remain intact, free of degradation. It may consist of a resin, e.g. made of sulfonated polystyrene-divinylbenzene, having for example a degree of crosslinking ranging between 1 and 5%. The resin is advantageously in the form of microbeads, the diameter of which preferably ranges between 450 and 550 nm. If the medium derived from the treatment with HF contains numerous products, it may be useful to optimize the resolution. To this end, the resin, e.g. made of sulfonated polystyrene-divinylbenzene may be packaged in the form of a column and may be completed, in its upper portion, with a layer of a material bearing positive charges, e.g. a primary amine salt, a secondary amine salt, a tertiary amine salt, a quaternary ammonium salt, or an ammonium group. This material may be in the form of beads advantageously having a diameter of 5 to 15 μm, e.g. approximately 10 μm. This material may be porous or nonporous. By way of example, it is indicated that a suitable material may consist of latex advantageously having a degree of crosslinking of 3 to 7%, e.g. approximately 5%.

The chromatography material (e.g. analytic column) marketed by the companies Dionex and Metrohm under the respective trademarks CARBOPAC™ (polystyrene cross-linked with divinylbenzene) agglomerated with quaternary ammonium functionalized latex beads) and Metrosep Carb satisfy the required criteria. This material is commonly referred to as being "of the CARBOPAC™ (polystyrene cross-linked with divinylbenzene) agglomerated with guaternary ammonium functionalized latex beads) type". The CARBOPAC™ PA1 ((polystyrene cross-linked with divinylbenzene) agglomerated with guaternary ammonium functionalized latex beads)) column is most particularly preferred.

Once the preparation derived from the treatment with HF has been loaded onto the chromatography column, elution is carried out with an eluting solution having a pH $\geq 12$, in particular so that the hydroxyl functions of the sugars ionize and are in the form of oxyanions which can be separated by anion exchange chromatography. If the PAD technique is subsequently used for detection, the eluting solution must also be compatible with this detection. In this regard, the eluting solution is advantageously free of carbonate.

Advantageously, the eluting solution is a sodium hydroxide solution, the molarity of which is between 10 and 300 mM, preferably between 20 and 150 mM, even more preferably between 40 and 100 mM.

The flow rate of the eluting solution depends on the type of column used, but is generally between 0.1 and 4 ml/min.

The specific oligosaccharides are detected on the chromatogram in the form of chromatography peaks having characteristic retention times under given operating conditions (same chromatography column, same solution and rate of elution, etc).

Finally, the oligosaccharide specific for the teichoic acid intended to be assayed is sought and quantified using a detection system, for example pulsed amperometric detection (PAD). This method of detection is based on the oxidation of the sugars on a working electrode, leading to the formation of an electric current which is measured. Regenerating and cleaning potential are often applied to the working electrode.

To determine the absolute amount of the teichoic acid intended to be assayed, results are advantageously related to a calibration curve established using a purified preparation of the teichoic acid in question, under the same conditions of treatment and analysis. According to a particular embodiment, the method according to the invention applies to the assaying of a teichoic acid in a preparation, which comes from a capsulated Gram+ bacterial culture, i.a. a preparation of Gram+ bacteria, which comprises one or more capsular polysaccharides. The method is particularly appropriated for the assaying of teichoic acids in a culture supernatant of capsulated Gram+ bacteria or in a preparation of purified capsular polysaccharide(s). In fact, due to the method of purification of these polysaccharides, which are usually prepared from a bacterial lysate, the purified preparations contain residual amounts of teichoic acid which it is advisable to assay.

The preparations of purified capsular polysaccharides may contain one or more polysaccharides in their free native form or may be in a form modified by partial depolymerization, activation or conjugation to a carrier peptide or protein such as tetanus toxoid or diphtheria toxoid. According to an embodiment of particular interest, the method according to the invention applies to the assaying of teichoic acids of *Streptoccocus pneumonaie*; and in particular, in a preparation containing one or more capsular polysaccharides of *Streptococcus pneumonaie*.

Pneumococci (*Streptococcus pneumonaie*) are capsulated Gram+ bacteria responsible for pathological infections, in particular for meningitis, bronchitis, rhinitis and otitis with complications in adults as in children. The pneumococci are divided up into serotypes depending on the structure of the polysaccharides, which form the capsule. Pneumococcal serotyping is carried out using a battery of immune sera, each immune serum being specific for a single type of capsular polysaccharide (monospecific immune sera). More than 90 different serotypes have been listed to date.

The vaccines against pneumococcus which are currently marketed all contain capsular polysaccharides. The purification of polysaccharides, being carried out from a bacterial lysate, these vaccines contain residual amounts of teichoic acids which it is advisable to assay.

The capsular polysaccharides of *Streptococcus pneumonaie* may in particular be chosen among those which are from the 23 serotypes (valences), which usually infect human beings; namely serotypes 1, 2, 3, 4, 5, 6B, 7F, 8, 9N, 9V, 10A, 11A, 12F, 14, 15B, 17F, 18C, 19A, 19F, 20, 22F, 23F and 33F.

By virtue of the assaying method according to the invention, it is in particular possible to quantify the pneumococcocal teichoic acids in any preparation containing one or more capsular polysaccharide(s), whatever the number and the serotype. The preparation may in particular contain one or more purified capsular polysaccharides in a free native form or in a modified form wherein the chemical structure of the polysaccharides exhibit similarities with those of the teichoic acids. These are polysaccharides of serotypes 6B, 10A, 17F, 19A, 19F and 20. In fact, the presence of the capsular polysaccharides of the abovementioned serotypes, the hydrolysis of which under the conditions of the invention leads to the production of specific oligosaccharides, has no effect on the assaying of the teichoic acids.

The method according to the invention applies to the assaying of teichoic acids in a preparation containing one or more capsular polysaccharides of serotype 6B, 10A, 17F, 19A, 19F or 20.

The preparation may also contain one or more polysaccharides of serotype 11A, 15B, 18C or 23F. Briefly, the preparation may contain the polysaccharides of the 23 most widespread serotypes or any possible combination based on these 23 serotypes. By way of example, such a preparation may contain the polysaccharides of serotypes 4, 6B, 9V, 14, 18C, 19F and 23F. It may also contain one or more of the additional polysaccharides of serotypes 1, 3, 5 and 7F.

By way of indication, the following remarks are submitted:

The oligosaccharides specific for the C-polysaccharide and for lipoteichoic acid, which are released during the treatment with HF under cold conditions according to the invention, are identical. In fact, the two teichoic acids have the same repeating unit. It is not therefore possible to assay the C-polysaccharide and lipoteichoic acid separately.

The capsular polysaccharides of serotypes 6B, 10A, 17F, 19A, 19F and 20, in which the linking together of the repeating units involves phosphodiester bonds, are degraded essentially in the form of specific oligosaccharides.

The capsular polysaccharides of serotypes 11A, 15B, 18C and 23F, the phosphodiester bonds of which are not directly involved in the linking together of the repeating units, cannot be hydrolyzed in the form of specific oligosaccharides. When subjected to the treatment with HF, they can however partially and randomly depolymerize to heterogeneous products, including in particular molecules such as glycerol or choline, and monosaccharides.

Finally, the other capsular polysaccharides which do not contain any phosphate groups are not depolymerized or are partially and randomly depolymerized to give, after treatment with HF, heterogeneous products, mainly of high molecular weight, which are nonidentifiable and nonquantifiable, and also a minor component of monomers and monosaccharides.

In fact, the medium derived from the treatment with HF may be more or less complex depending on the number and the type of capsular polysaccharide present at the start. It is therefore advisable to separate the teichoic acid-specific oligosaccharide from the other hydrolysis products (monomers, monosaccharides, unhydrolyzed or partially hydrolyzed polysaccharides, etc.).

Surprisingly, the oligosaccharide specific for the teichoic acids of *Streptococcus pneumonaie* behaves like a monosaccharide when it is analyzed and separated by the HPAEC-PAD technology. It distinguishes itself from the behaviour of the oligosaccharides of capsular polysaccharides. In order to separate it and quantify it by HPAEC-PAD with particular resolution, the use of a CarboPac PA1™ chromatography column and a 75 mM isocratic sodium hydroxide solution are recommended. Under these conditions, the chromatography peak corresponds to a retention time of 4.30 min±10% when the flow rate of the eluting solution is 1 ml/min. The surface area of the chromatography peak reflects the relative amount of C-polysaccharide and of lipoteichoic acid present in the preparation.

In the context of the use of the assaying method of teichoic acids according to the invention, it was discovered that *Streptococcus pneumonaie* serotype 5 does not possess any C-polysaccharide. On the other hand, a teichoic acid, referred to as C5-polysaccharide, is found, which substitutes for this. The formula of its repeating units differs slightly from that of the C-polysaccharide. It is as follows:

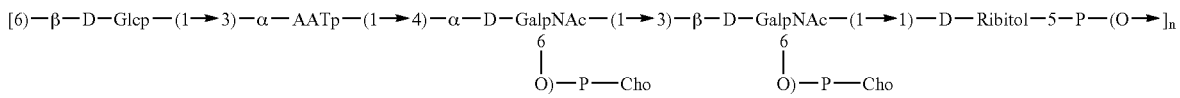

For this reason, according to a very particular method, the invention also applies to the assaying of the C5-polysaccharide, in particular in a preparation containing the capsular polysaccharide of *Streptococcus pneumonaie* serotype 5. The procedure described above for assaying the C-polysaccharide and lipoteichoic acid is also suitable for assaying the C5-polysaccharide. Its chromatography peak has, under these conditions, a retention time of 3.30 min±10%.

To determine the residual absolute amounts of teichoic acid, reference is made to standard curves produced from "stock" preparations expressing known amounts as a function of the surface areas of the chromatography peaks.

For example, the residual absolute amounts of C-polysaccharide and lipoteichoic acid can be determined using a preparation of purified C-polysaccharide, such as the one marketed by Staten Serum Institute, Danemark (example 1).

To determine the residual absolute amounts of C5-polysaccharide, it is advisable to use as "stock" preparation, a purified preparation of C5-polysaccharide, which comes from a lysate or a culture supernatant of serotype 5 pneumococci. In a first step, the polysaccharide fraction is extracted by one or several fractionated alcohol precipitations. The main contaminants, i.a. proteins and nucleic acids are then discarded from the preparation. The polysaccharide fraction free of its main contaminants is then submitted to a size exclusion chromatography to separate the C5-polysaccharide from the other polysaccharides. The chromatography process described in example 1 can be applied. The process of polysaccharide extraction by fractionated alcohol precipitation, and the elimination process of protein and nucleic acids contaminants are well known processes of a person skilled in the art. Notably, one may refer to the processes described in U.S. Pat. No. 4,686,102.

The C5-polysaccharide preparation thus purified, may be used as a "standard" to determine residual absolute amounts of C5-polysaccharide according to the assaying method of the invention; but more generally, it can be used in any assaying method of the C5-polysaccharide, which refers to a standard curve.

Accordingly, the invention relates to the use of a purified C5-polysaccharide having a repeating unit of formula:

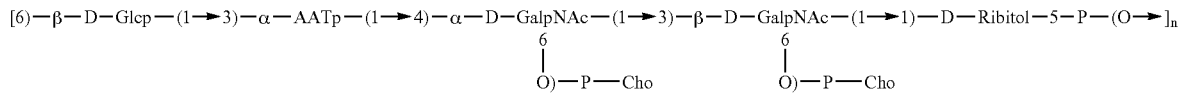

for establishing a standard curve intended for assaying the C5-polysaccharide, in a preparation comprising a capsular polysaccharide of *Streptococcus pneumonaie* serotype 5.

The present invention will be understood more clearly in light of the following examples which serve to illustrate the invention without, however, limiting the content thereof.

FIG. 1 represents the HPAEC-PAD chromatogram, after treatment with HF, of the Pneumo 23™ vaccine containing the capsular polysaccharides of serotypes 1, 2, 3, 4, 5, 6B, 7F, 8, 9N, 9V, 10A, 11A, 12F, 14, 15B, 17F, 18C, 19A, 19F, 20, 22F, 23F and 33F. The peaks with an above them correspond to the monosaccharides originating from the hydrolysis of the capsular polysaccharides. The Rib peak corresponds to ribitol. The Fru peak corresponds to fructose (internal standard). The oligo C and oligo C5 peaks correspond, respectively, to the specific oligosaccharides C and C5.

Figure 2:
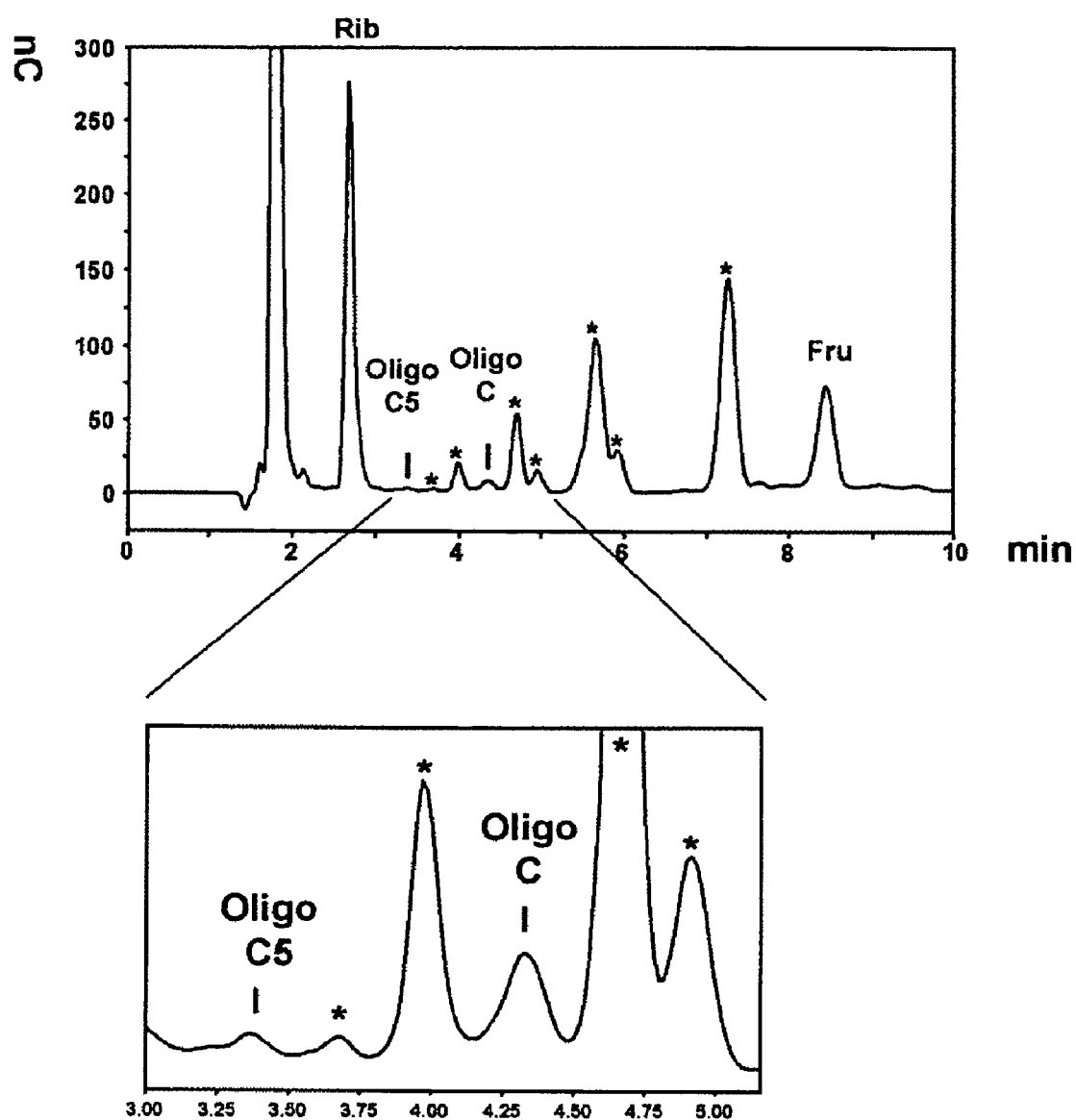

FIG. 2 represents the HPAEC-PAD chromatogram, after treatment with HF, of a vaccine formulation F3 as described in WO 98/51339, containing the Tt and Dt conjugates of the capsular polysaccharides of serotypes 1, 3, 4, 5, 6B, 7F, 9V, 14, 18C, 19F and 23F of pneumococcus.

EXAMPLE 1

Assaying of the Residual Amounts of C-polysaccharide and C5-polysaccharide in the Pneumo 23™ Vaccine Containing the Capsular Polysaccharides of Serotypes 1, 2, 3, 4, 5, 6B, 7F, 8, 9N, 9V, 10A, 11A, 12F, 14, 15B, 17F, 18C, 19A, 19F, 20, 22F, 23F and 33F of Pneumococcus 1.1. Stock Solutions for Standard Range 1.1.1. C5-polysaccharide:

This polysaccharide is purified as described in the following paragraph, from a preparation of capsular polysaccharide of pneumococcus serotype 5, obtained by fractionated alcoholic precipitation of a pneumococcus serotype 5 lysate, followed by a phenolic extraction to remove the proteins, by a fractionated precipitation in the presence of calcium chloride to remove the nucleic acids and, finally, by a second fractionated alcoholic precipitation. The precipitate obtained is washed with absolute alcohol and then dried under vacuum. The desiccate is resolubilized at a concentration of 10 mg/ml in a 200 mM NaCl buffer.

4 ml of this solution are loaded onto a chromatography column (90 cm×1.6 cm in diameter) containing sepharose-CL 4B gel. The column is subjected a flow of 200 mM NaCl solution at a flow rate of 0.6 ml/min in order to separate the C5-polysaccharide from the capsular polysaccharide. The eluate is collected in fractions. The UV absorbance at 206 nm of each fraction is measured. This makes it possible to identify two series of clearly distinct fractions: the first containing the type 5 capsular polysaccharide; the second, eluted, containing the C5-polysaccharide. This second series of fractions is dialyzed against distilled water, concentrated using a rotary evaporator, and then conserved in the form of a lyophilisate. The degree of purity of the lyophilisate is approximately 70%.

Subsequently, the exact amount of C5-polysaccharide in the preparation thus obtained is determined by assaying the ribitol released after hydrolysis.

The lyophilisate is resolubilized in ultrafiltered purified water, in a proportion of 10 µg/ml (dry weight).

In parallel, a standard range of ribitol of 0 to 4 µg/ml is prepared in ultrafiltered purified water. To control the reproducibility of the chromatography, a fixed amount of mannose, which acts as an internal standard, can be added to all the samples.

400 µg of the solution of C5-polysaccharide prepared above are dried under nitrogen. The desiccate is treated with 200 µg of 48% hydrofluoric acid for 2 hours at 65° C. The mixture is dried and 400 µg of 2N trifluoroacetic acid are added for 2 hours at 135° C. The mixture is dried under a stream of nitrogen.

For analysis by HPAEC-PAD chromatography, the desiccates obtained in the preceding step are dissolved in 400 µl of ultrafiltered purified water. An aliquot of 100 µl of each of the solutions is injected onto a CARBOPAC MA1 analytical column (4×250 mm) (DIONEX # 44066) pre-equilibrated with a 480 mM sodium hydroxide solution. The column is subjected to a flow of 480 mM sodium hydroxide solution for 60 minutes at a flow rate of 0.4 ml/min in order to elute the neutral monosaccharides such as ribitol and mannose. The column temperature is maintained at 30° C.

Under these conditions, the chromatography peak corresponding to the ribitol appears at 19.9±5% min, while the peak corresponding to the mannose (internal standard) appears at 25.2±5% min.

The standard curve (amount of ribitol as a function of the surface area of the peaks) is then established. The amount of ribitol contained in the starting preparation is determined by interpolation. Next, the exact amount of C5-polysaccharide is then deduced, in the knowledge that the repeating unit of the C5-polysaccharide consists of 11.1% (w/w) of ribitol.

1.1.2. C-polysaccharide:

The purified C-polysaccharide powder (Staten Serum Institute, Denmark) is dissolved in ultrapurified water, and then its concentration the concentration of C-polysaccharide is adjusted to 10 µg/ml on the basis of the ribitol assay carried out according to the same method as that for which details are given in paragraph 1.1.1.

1.2. Standard Ranges:

From 0 to 5 µg/ml of precisely assayed teichoic acids, prepared from the stock solutions by dilution in ultrafiltered purified water. The samples for the range are then dried under nitrogen.

1.3. Preparation of the Sample to be Assayed 3 vaccine doses (1.5 ml) are dialyzed against distilled water, and the dialysate is then lyophilized. The lyophilizate is then taken up with 1.5 ml of ultrafiltered purified water, from which an aliquot of 40 µl is taken, which is then dried under nitrogen.

To control the reproducibility of the chromatography, a fixed amount of fructose, which serves as an internal standard, can be added to the sample to be analyzed.

1.4. Hydrolysis with HF

All the desiccates (sample to be assayed and samples for the standard range) are treated with 400 μl of 48% hydrofluoric acid for 48 hours at 5° C. Drying is carried out under a stream of nitrogen and the dried material is taken up with 400 μl of ultrafiltered purified water at the time of analysis.

1.5. Analysis by HPAEC-PAD Chromatography

100 μl of each of the hydrolysates are injected onto a CARBOPAC PA1 analytical column (4×250 mm) (DIONEX #35391) pre-equilibrated with a 75 mM sodium hydroxide solution. The column is subjected to a flow of 75 mM sodium hydroxide solution for 10 min at a flow rate of 1 ml/min in order to elute the C-polysaccharide-specific and C5-polysaccharide-specific oligo-saccharides and also the monosaccharides which are neutral at the pH of the analysis. The column temperature is maintained at 30° C. To finish off the chromatography, a 75 mM sodium hydroxide solution containing sodium acetate is gradually added in order to elute all the remaining monosaccharides, oligosaccharides and polysaccharides.

Under these conditions, the chromatography peak corresponding to the ribitol released during hydrolysis of the C-polysaccharide, of the C5-polysaccharide and of the 6B and 10A capsular polysaccharides appears at 2.65±5% min. The peaks corresponding to the C5-polysaccharide-specific and C-polysaccharide specific oligosaccharides, and also the fructose peak (internal standard), appear, respectively, at 3.30±5% min, 4.30±5% and 8.5±5% min (see FIG. 1).

The standard curves (amount of C-polysaccharide or C5-polysaccharide as a function of the surface area of the peaks) is established. The amounts of C-polysaccharide and C5-polysaccharide present in the starting preparation are determined by interpolation.

EXAMPLE 2

Assaying of the Residual Amounts of C-polysaccharide and C5-polysaccharide in the Vaccine Formulation F3 as Described in WO 98/51339, Containing the Dt and/or Tt Conjugates of the Capsular Polysaccharides of Serotypes 1, 3, 4, 5, 6B, 7F, 9V, 14, 18C, 19F and 23F of Pneumococcus The same protocol as that described in paragraph 1.3 is used to prepare the sample to be assayed. The volume of the aliquot taken is 1 ml here. The chromatographic profile obtained is that shown in FIG. 2.

What is claimed is:

1. A method for quantifying the teichoic acids in a preparation comprising teichoic acids and one or more additional capsular polysaccharides of *Streptococcus pneumoniae*, the method comprising:
   (i) treating the preparation with hydrofluoric acid (HF) at a temperature of less than or equal to 40° C., in order to release the oligosaccharides specific for the teichoic acids present in the preparation; and
   (ii) quantifying the specific oligosaccharides obtained in (i).

2. The method as claimed in claim 1, in which the preparation is treated with hydrofluoric acid (HF) at a temperature from 0° C. to 20° C.

3. The method as claimed in claim 2, in which the preparation is treated with hydrofluoric acid (HF) at a temperature from 4° C. to 20° C.

4. The method as claimed in claim 2, in which the preparation is treated with hydrofluoric acid (HF) at a final concentration of from 10 to 73% (weight/weight).

5. The method as claimed in claim 4, in which the preparation is treated with hydrofluoric acid (HF) at a final concentration of between 40 and 60%.

6. The method as claimed in claim 5, in which the preparation is treated with hydrofluoric acid (HF) at a final concentration of between 45 and 50%.

7. The method as claimed in claim 1, wherein the specific oligosaccharides are quantified using a technique which makes it possible to quantify the monosaccharides.

8. The method as claimed in claim 7, in which the specific oligosaccharides are quantified using high performance anion exchange chromatography (HPAEC), optionally coupled with pulsed amperometric detection (PAD).

9. The method as claimed in claim 8, in which the HPAEC uses a support compatible with a pH greater than or equal to 12.

10. The method as claimed in claim 9, in which the support consists of sulfonated polystyrene-divinylbenzene.

11. The method as claimed in claim 10, in which the sulfonated polystyrene-divinylbenzene has a degree of crosslinking of 1 to 5%.

12. The method as claimed in claim 11, in which the sulfonated polystyrene-divinylbenzene is in the form of microbeads having a diameter of 450 to 550 nm.

13. The method as claimed in claim 12, in which the chromatography support is packaged in the form of a column and is completed, in its upper part, by a layer of a material bearing positive charges for optimizing the column resolution.

14. The method as claimed in claim 13, in which the material for optimizing the resolution consists of material bearing a primary amine salt, a secondary amine salt, a tertiary amine salt, a quaternary ammonium salt, or an ammonium group.

15. The method as claimed in claim 14, in which the material is latex having a degree of crosslinking of 3 to 7%.

16. The method as claimed in claim 8, in which the HPAEC uses a material of the CARBOPAC™ ((polystyrene cross-linked with divinylbenzene) agglomerated with guaternary ammonium functionalized latex beads)) type.

17. The method as claimed in claim 16, in which the material is a CARBOPAC™ PA1 ((polystyrene cross-linked with divinylbenzene) agglomerated with quaternary ammonium functionalized latex beads)) chromatographic column.

18. The method as claimed in claim 8, in which the HPAEC uses an eluting solution having a pH≧12.

19. The method as claimed in claim 18, in which the eluting solution is free of carbonate.

20. The method as claimed in claim 19, in which the eluting solution is a sodium hydroxide solution, the molarity of which is between 10 and 300 mM.

21. The method as claimed in claim 20, in which the sodium hydroxide solution has a molarity of between 40 and 100 mM.

22. The method as claimed in claim 1, in which the preparation comprises one or more capsular polysaccharides of *Streptococcus pneumoniae* serotype 6B, 10A, 17F, 19A, 19F or 20.

23. The method as claimed in claim 22, in which the preparation comprises a capsular polysaccharide of each one of *Streptococcus pneumoniae* serotypes 6B, 10A, 17F, 19A, 19F and 20.

24. The method as claimed in claim 1, the method comprising:
   (i) treating the preparation with hydrochloric acid (HF) at a temperature of less than or equal to 40° C., in order to release the teichoic acid-specific oligosaccharide present in the preparation, said specific oligosaccharides comprising the oligosaccharide specific for the C5-polysaccharide; and (ii) quantifying the oligosaccharide specific for the C5 polysaccharide obtained in (i).

25. The method as claimed in claim 24, in which the preparation contains a capsular polysaccharide of *Streptococcus pneumoniae* serotype 5.

* * * * *